(12) United States Patent
Rantala et al.

(10) Patent No.: US 8,512,273 B2
(45) Date of Patent: Aug. 20, 2013

(54) AUTOMATIC CALIBRATION OF THE SENSITIVITY OF A SUBJECT TO A DRUG

(75) Inventors: Tor Borje Rantala, Helsinki (FI); Morkku Paloheimo, Espoo (FI)

(73) Assignee: General Electric Company, Schenectady, NY (US)

( * ) Notice: Subject to any disclaimer, the term of this patent is extended or adjusted under 35 U.S.C. 154(b) by 263 days.

(21) Appl. No.: 11/680,328

(22) Filed: Feb. 28, 2007

(65) Prior Publication Data
US 2007/0208322 A1 Sep. 6, 2007

(30) Foreign Application Priority Data
Mar. 6, 2006 (EP) .................................. 06004450

(51) Int. Cl.
*A61M 31/00* (2006.01)
*A61B 81/00* (2006.01)

(52) U.S. Cl.
USPC ............... 604/23; 604/65; 604/512; 600/545

(58) Field of Classification Search
USPC ............... 604/23, 24, 26, 65, 500, 512, 514; 600/300, 544, 545; 128/910
See application file for complete search history.

(56) References Cited

U.S. PATENT DOCUMENTS

| | | | | |
|---|---|---|---|---|
| 2,888,922 A * | 6/1959 | Bellville | .................. | 128/204.23 |
| 4,280,494 A * | 7/1981 | Cosgrove et al. | ............. | 604/503 |
| 5,131,401 A * | 7/1992 | Westenskow et al. | ........ | 600/554 |
| 5,455,161 A * | 10/1995 | Assaraf et al. | ............... | 435/7.23 |
| 6,016,444 A * | 1/2000 | John | ............................. | 600/544 |
| 6,371,922 B1 * | 4/2002 | Baumann et al. | ............. | 600/485 |
| 7,171,263 B2 * | 1/2007 | Darvish et al. | .................. | 604/20 |
| 7,198,906 B2 * | 4/2007 | Machida et al. | ................ | 435/32 |
| 7,247,154 B2 * | 7/2007 | Hickle | ........................ | 604/500 |
| 2002/0042563 A1 * | 4/2002 | Becerra et al. | ................ | 600/407 |
| 2002/0107504 A1 * | 8/2002 | Gordon | ........................ | 604/507 |
| 2002/0173729 A1 * | 11/2002 | Viertio-Oja et al. | .......... | 600/544 |
| 2003/0055355 A1 * | 3/2003 | Viertio-Oja | ................... | 600/544 |

(Continued)

FOREIGN PATENT DOCUMENTS

| EP | 0 774 234 A | | 5/1997 |
|---|---|---|---|
| WO | WO 2004/112603 | * | 12/2004 |

(Continued)

OTHER PUBLICATIONS

Ryu et al., Fractionated Irradiation Leads to Restoration of Drug Sensitivity in MDR Cells that Correlates with Down-regulation of P-gp and DNA-Dependent Protein Kinase Activity, 2004, Radiation Research 162, 527-535.*

(Continued)

*Primary Examiner* — Kevin C Sirmons
*Assistant Examiner* — William Carpenter
(74) *Attorney, Agent, or Firm* — Global Patent Operation

(57) ABSTRACT

A method, a system, and a computer program for calibration of sensitivity of a subject to a drug. The subject is delivered with the drug at a delivery rate and a signal responsive to the drug is measured from the subject. When determining the sensitivity of the subject to the drug in question, a change in the delivery rate of the drug is initiated. The change in the delivery rate causes a small change in the signal responsive to the drug. The change in the measured signal caused by the drug delivery rate change is detected, and the sensitivity of the patient is determined.

9 Claims, 3 Drawing Sheets

(56) References Cited

U.S. PATENT DOCUMENTS

| | | | |
|---|---|---|---|
| 2003/0113831 A1* | 6/2003 | Hakonarson | 435/29 |
| 2004/0204656 A1* | 10/2004 | Tolvanen-Laakso et al. | 600/544 |
| 2005/0010166 A1* | 1/2005 | Hickle | 604/66 |
| 2005/0267440 A1* | 12/2005 | Herman et al. | 604/501 |
| 2006/0009733 A1* | 1/2006 | Martin | 604/65 |
| 2007/0015972 A1* | 1/2007 | Wang et al. | 600/300 |
| 2007/0065363 A1* | 3/2007 | Dalal et al. | 424/9.1 |
| 2007/0118075 A1* | 5/2007 | Uutela et al. | 604/65 |

FOREIGN PATENT DOCUMENTS

| | | | |
|---|---|---|---|
| WO | WO 2004/112603 A | | 12/2004 |
| WO | WO 2005/072792 | * | 8/2005 |
| WO | WO 2005/072792 A | | 8/2005 |

OTHER PUBLICATIONS

Ihmsen H et al: "Development of acute tolerance to the EEG effect of propofol in rats", British Journal of Anaesthesia vol. 95, No. 3, Sep. 2005, pp. 367-371, XP002397962 ISSN 0007-0912.

* cited by examiner

AUTOMATIC CALIBRATION OF THE SENSITIVITY OF A SUBJECT TO A DRUG

FIELD OF THE INVENTION

The invention relates to a method, apparatus, and computer product for calibrating the sensitivity of a subject to a drug. According to the invention, the sensitivity of the subject to a drug is determined by detecting the change in a signal measured from the subject caused by blood or effect site concentration change of a drug.

BACKGROUND OF THE INVENTION

Demanding medical procedures often require the subject or the patient to be unaware of the procedure. In such surgeries, the patient is anesthetized to achieve a total loss of consciousness and sensation so that the surgery can be conducted without the patient being aware of it. Anesthesia is achieved by anesthetic drugs which are well known for having a potent effect on the brain cell system. The drug can be given to the patient in one bolus injection or it can be given continuously through a motor driven syringe pump or through an electronic anesthetic gas vaporizer via an anesthetic mask or endotracheal tube. When administration of the drug is by inhalation, the anesthetic agent comprises a volatile liquid that is vaporized in a vaporizer. The vaporized anesthetic agent is entrained in the breathing gases for the patient.

Usually, the effect of an anesthetic drug is short-term e.g. a few minutes because it is important that the patient goes under anesthesia quickly and awakes shortly after the surgery. When the drug is given constantly to the patient the duration of anesthesia can be controlled by adding the anesthetic drug as long as needed.

The extent to which the patient is anesthetized is often termed "adequacy of anesthesia". As the magnitude of anesthetization increases, the anesthetized patient typically fails to respond to spoken commands, he loses reflexes and undergoes depression of vital signs, and the like. Anesthesia can be considered to comprise of three attributes: unconsciousness i.e. hypnosis, loss of pain sensation i.e. analgesia and muscular relaxation. Sufficient muscular relaxation is important for the surgeon for example to be able to access the target part of the body without unnecessarily cutting through the muscles. When the neuromuscular junction is blocked by giving such drugs to the patient, the muscles do not respond to movement commands from the motor nerves.

Monitoring the depth of anesthesia is important when assuring that the patient remains unconscious and without sensations during the whole time of the surgery. Typically, the depth of anesthesia is wanted on a certain level depending on the procedure and each phase of the procedure. For example, at the beginning of the operation, a very heavy level of anesthetization is needed, whereas at the end when the surgeon is left with stitching up the wound, the anesthesia level can be brought up to a state of less deep sleep. Therefore, to be able to adjust the depth of anesthesia, its existing level in the patient is sensed and used to control the anesthetic drug administration to the patient. This manner of controlling the given amount of drug to achieve and maintain a desired level in the patient is called closed loop, or feedback, administration of anesthetic drug.

The importance of controlling the adequate anesthesia level is essential in common clinical practice and it is therefore a subject of constant attention and research. Inadequate anesthesia may result in the patient knowing or sensing stages of the procedure and as a consequence, obtain traumatic experiences. Excessively deep anesthetization on the other hand prolongs the recovery from the anesthetization and causes nausea and queasiness. In addition, most anesthetic drugs are expensive and their excessive use should, therefore, be avoided.

Another reason for the rising interest to monitor depth of anesthesia is its difficulty. Anesthetic agents manipulate the state of the patient's brain and these alterations of the brain are not easy to detect. However, it has long been known that the neurological activity of the brain is reflected in biopotentials available on the surface of the brain and on the scalp. Thus, efforts to quantify the extent of anesthesia induced hypnosis have turned to a study of these biopotentials. The biopotential electrical signals recorded on the scalp comprise an electroencephalogram (EEG). Several different methods for determining the hypnotic state based on the measured EEG signal have been introduced in literature. Among these are e.g. deriving from the EEG signal a bispectral index (BIS) that correlates behavioral assessments of sedation and hypnosis. Another recently obtained signal derived from the EEG is the entropy signal which describes the irregularity of the EEG and FEMG (frontalis electromyography) signals.

Entropy, as a physical concept, describes the state of disorder of a physical system. When used in signal analysis, entropy addresses and describes the complexity, unpredictability, or randomness characteristics of a signal. In a simple example, a signal in which sequential values are alternately of one fixed magnitude and then of another fixed magnitude has an entropy of zero, i.e. the signal is predictable. A signal in which sequential values are generated by a random number generator has greater complexity and a higher entropy.

Applying the concept of entropy to the brain, the premise is that when a person is awake, the mind is full of activity and hence the state of the brain is more complex, and noise like. Since EEG signals reflect the underlying state of brain activity, this is reflected in relatively more randomness and complexity in the EEG signal data and therefore, higher entropy. As a person falls asleep or is anesthetized, the brain function begins to lessen and becomes more orderly and regular and has, therefore, lower entropy. Similarly to EEG, the frontalis electromyography (FEMG) signal quiets down as the deeper parts of the brain are increasingly saturated with anesthetics.

Each patient has a unique way of responding to the drug. The amount of drug that totally knocks out a smaller patient, might not cause a heavier patient anything more than a funny feeling. Also, drug abusers might have developed a special resistance to drugs. The unique process by which a drug, such as an anesthetic drug, takes its effect in the body, has two important aspects: pharmacokinetics and pharmacodynamics. Pharmacokinetics deals with the effect of the distribution of the drug, such as the body's absorption, transport or diffusion, metabolism, and excretion of the drug. Pharmacodynamics describes how the drug is affecting a particular organ where the drug is supposed to have its effect.

Traditionally, determining the level of anesthesia has been dependent on the doctor's experience and professional skill. Adequacy of anesthesia is routinely assessed by subjectively observing the patient's clinical signs, such as heart rate, blood pressure, lacrimation, sweating and movement. However, these indices give an indirect indication of the actual state of consciousness. This method for determining the adequacy of anesthesia is neither suitable if the procedure requires heavy muscle relaxants e.g. abdominal surgery. In these kind of operations observing the patient's responses to external stimuli is completely inadequate to determine the level of anesthesia. In the worst case scenario, the patient is given strong muscle relaxants and is, therefore, immobile but is actually awake and aware of the surgery the whole time whereas the medical staff believes him to be heavily anesthetized. To prevent such traumas, the adequate level of anesthesia becomes even more important.

Since the anesthesia level is dependent on the amount of drug given to the patient, the depth of anesthesia can be controlled by adjusting the infusion rate of the drug. Adjusting the depth of anesthesia is based on the anesthesiologist's professional skill when he/she estimates how much a certain change in the infusion rate of the anesthetic drug affects the depth of anesthesia. Traditionally, the anesthesiologist adjusts the level of anesthesia e.g. by reducing the infusion rate of the drug to achieve a less deep state of sleep, and if the anesthesia level is too light (closer to the awake state), the anesthesiologist increases the infusion rate until the desired anesthesia level is achieved. Analogously, if anesthesia should be deepened, the anesthesiologist increases the infusion rate until the desired anesthesia level is reached.

The problem when adjusting the anesthesia level is that the only way to find out the effect of an increase or a decrease in the infusion rate is to test it and observe the response the infusion rate change has on the anesthesia level. Due to the unique way each patient responds to a drug and due to the differences in how the drug accumulates in the patient's body over time, it is difficult to know how much a change in the infusion rate actually changes the anesthesia level at each moment.

SUMMARY OF THE INVENTION

The invention relates to a method for calibrating the sensitivity of a subject or a patient to a drug. In the method, the subject of a medical procedure is delivered with the drug at a delivery rate, and a signal from the subject is measured as an indication of the subject's response to the given drug. The measured signal can be any signal that is responsive to the given drug. To be able to determine the sensitivity of the subject to the drug in question, the subject is given small additional boluses of the drug, or the drug delivery rate is changed momentarily. The change in the drug delivery rate can also be negative, so that the delivery rate is momentarily reduced. This change in the delivery rate causes a small change in the signal responsive to the drug. By detecting the change in the measured signal caused by the drug delivery rate change, the sensitivity of the subject at that moment can be determined.

The invention also relates to a system for calibration of sensitivity of a subject to a drug, the system comprising: means for delivering the subject constantly with a drug at a delivery rate, means for initiating a change in the delivery rate of the drug to the subject, means for measuring a signal responsive to the drug from the subject, means for detecting a change in the measured signal resulting from the change in the delivery rate of the drug, and means for calculating the sensitivity of the subject to the drug based on the change in the measured signal.

The invention further relates to a computer program comprising code adapted to perform the following steps when executed on a data processing device for calibration of sensitivity of a subject to a drug: delivering the subject constantly with the drug, initiating a change in the delivery rate of the drug to the subject, measuring a signal responsive to the drug from the subject, detecting a change in the measured signal resulting from the change in the delivery rate of the drug, and calculating the sensitivity of the subject to the drug based on the change in the measured signal. In one embodiment of the invention, the sensitivity of the subject is calculated based on the ratio between the change in the measured signal and the change in the delivery rate.

In another embodiment of the invention, said measured signal responsive to the drug is a signal describing the depth of anesthesia.

In another embodiment of the invention, said measured signal responsive to the drug is derived from an electroencephalogram (EEG) signal.

In another embodiment of the invention, said signal responsive to the drug is entropy or bispectral index.

In another embodiment of the invention, said signal responsive to the drug is blood pressure.

In another embodiment of the invention, said signal responsive to the drug is a signal describing muscle relaxation.

In another embodiment of the invention, initiating the calibration of the subject's sensitivity to a drug is done automatically, by a user and/or by the user based on a given suggestion.

In another embodiment of the invention, said calibration of the subject's sensitivity to a drug is done by calibrating the subject's sensitivity to a drug at given intervals.

In another embodiment of the invention, safety limits are set so that the subject is never given the drug over the safety limit.

The benefits of the invention are related to the improved patient safety and reliability in adjusting anesthesia level during complex surgery. During different stages of the operation, the level of anesthesia can be changed precisely and reliably, each state being optimal for each phase of the operation. A further benefit of the invention is that it allows the anesthesiologists to concentrate on more important matters than adjusting and estimating the correct infusion rate to achieve the desired anesthesia level.

Various other features, objects, and advantages of the invention will further be apparent from the following detailed description and the drawings.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

PURPOSE OF THE INVENTION

The purpose of the invention is to provide a reliable method for calibrating and estimating the sensitivity of a patient to a drug.

DETAILED DESCRIPTION OF THE EMBODIMENTS

Reference will now be made in detail to the embodiments of the present invention, examples of which are illustrated in the accompanying drawings.

Figure 1:
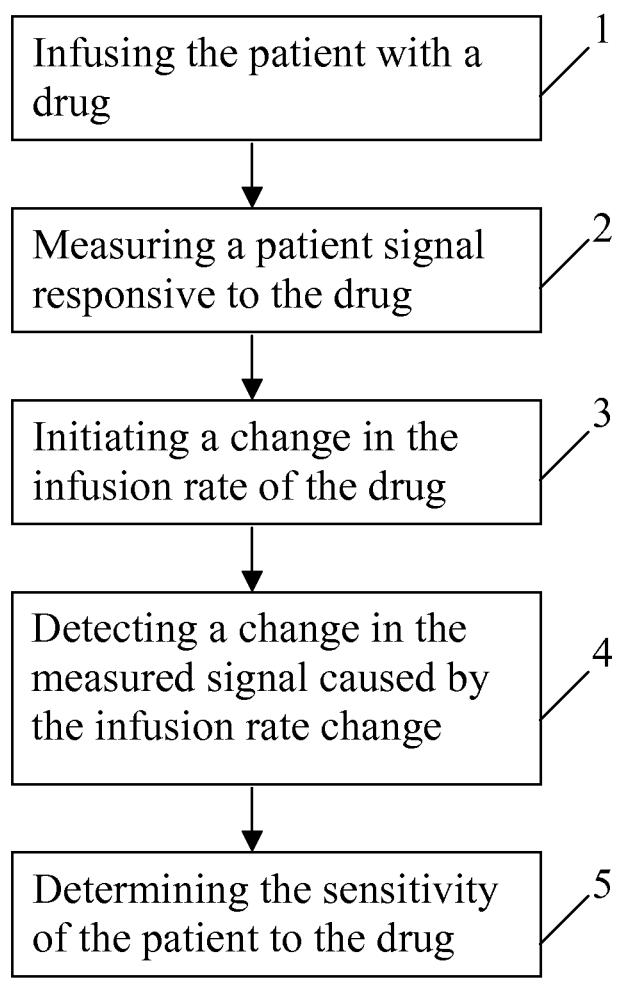
FIG. 1 is a flow chart depicting an embodiment of the method for calibrating the sensitivity of the patient.

An embodiment of the method for calibrating the sensitivity of the patient is depicted in a block diagram in FIG. 1. In the method, the patient is given a drug by infusion at an infusion rate I and the response of the patient to the drug is measured 2. The drug may be any drug that has a measurable effect on the patient, e.g. a blood pressure drug, an anesthetic drug or a muscle relaxant or such. The measured signal can be any signal that is responsive to the given drug. For example, when giving muscle relaxants, electromyogram (EMG) of the patient is measured from a chosen part of the body or in the case of an anesthetic drug, the depth of anesthesia is measured.

To be able to determine the sensitivity of the patient to the drug in question, the patient is given small additional boluses of the drug and/or the infusion rate of the drug is added momentarily 3. The momentary change in the drug infusion rate as well as a single bolus of the drug have an effect on the measured signal. The initiated change in the infusion rate may also be negative, thus causing an opposite change in the response signal. The change in the measured signal caused by the infusion rate change is detected 4 and, the sensitivity of the patient to the drug at that moment determined 5. Since the sensitivity of the patient is calculated based on a change in the measured signal caused by a blood or effect site concentration change of a drug, it can be calculated every time there is a change in the delivery of the drug.

Because the sensitivity of each patient to an anesthetic drug is unique, one can not accurately estimate how the patient reacts to the change in the infusion rate of the drug. It is therefore important to know the current sensitivity of the patient to the drug in question. Sensitivity varies as a function of time and it also depends on the state of the patient. Different parts of the body get saturated at different times and sensitivity may change rapidly e.g. when a certain compartment of the body saturates. Typically, in the beginning when none of the compartments of the body have saturated, sensitivity tends to be large. On the other hand, when the patient has been anesthetized for a while, sensitivity tends to decrease. Blood concentration rises quickly at the beginning of anesthesia until the drug reaches fat tissue and the brain. Therefore, after the drug has reached fatty tissue it continues to diffuse form the fatty tissue to the circulation and to the brain even if the patient is not given more of the anesthetic drug, and thus maintaining the anesthetic state.

Figure 2:
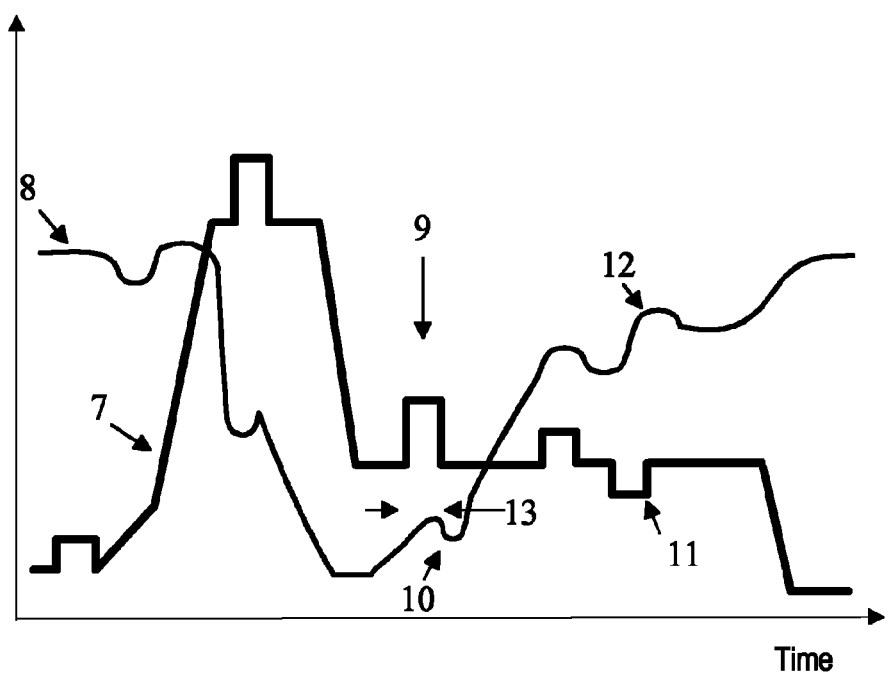
FIG. 2 is a diagram illustrating how an entropy signal responds to infusion rate changes.

FIG. 2 is a graph of infusion rate of a drug 7 and its effect on an entropy signal 8 during anesthesia. The entropy signal 8 describing anesthesia in FIG. 2 begins from 80%-100% (the EEG signal being random and the entropy high), and the patient is fully awake or he/she is slightly under sedatives. For the initial phase of the operation, usually intubation or first incision, the patient is given a large dose of the drug for the patient to reach a deeply unconscious state. This means usually about 20%-40% of entropy. The unit of entropy can be scaled from 0% of total unconsciousness (and a predictable EEG) to 100% of wide awake (and a random EEG). Closer to the end of the operation, the anesthesia level can be brought up again to a state of less deep sleep and start preparing for awakening.

The small peaks (e.g. 9, 11) in the infusion rate seen in FIG. 2 are small changes in the amount of drug or its infusion rate to the patient. These changes can be initiated automatically by the apparatus according to the present invention. The change in the infusion rate causes a change (e.g. 10, 12) in the response signal which is then detected. There is a delay 13 in the patient's response in the measured signal which might change a little during anesthetization. However, the system is able to learn the delay from previous calibration results and distinguish the change in the response signal caused by the infusion rate change from other factors causing small changes in the measured signal.

Sensitivity can be calculated as the ratio between the change in the measured signal and the infusion rate change. It may be determined by using the formula: DS (Sensitivity)= (change in the measured signal)/(infusion rate change) or when monitoring entropy signal: DS (Sensitivity)=(change in entropy)/(change in infusion rate). For example, the patient may be given a calibration bolus of 1 mg in addition to the steady infusion, if the measured entropy signal changes e.g. 10%, the sensitivity at that time is 10%/mg. At another time, the same bolus might cause e.g. a 20% change in the entropy signal and, therefore, give a sensitivity value of 20%/mg. It is also possible to calculate the sensitivity based on other filtered values derived from the signals or by determining the signal changes from their integrals by using the equation:

$$DS(\text{Sensitivity}) = \left( \int_{t1}^{t3} \text{Measured\_signal} \Big/ \int_{t0}^{t2} \text{Infusion\_rate} \right),$$

where $t_0$ is start time of the delivery rate change, $t_2$ is its end and $t_1$ is the delayed start of the effect in the measured signal and $t_3$ is its end.

The calibration of the sensitivity value may be initiated automatically by the apparatus, or the apparatus may suggest the user to initiate the calibration. The calibration may also be left completely to the user. It can be done at regular intervals or at randomly chosen moments. The sensitivity value may additionally be updated each time the anesthesiologist gives a bolus of the drug to the patient or changes the drug delivery rate to achieve a desired anesthesia level.

This sensitivity parameter can be shown to the user on a display device. The user may also input the desired anesthesia level and the apparatus calculates the appropriate bolus and/or infusion rate change to achieve this level. Instead of manually iterating the desired level of anesthesia, the anesthesiologist saves time and the patient reaches the desired anesthesia depth faster and more reliably.

Figure 3:
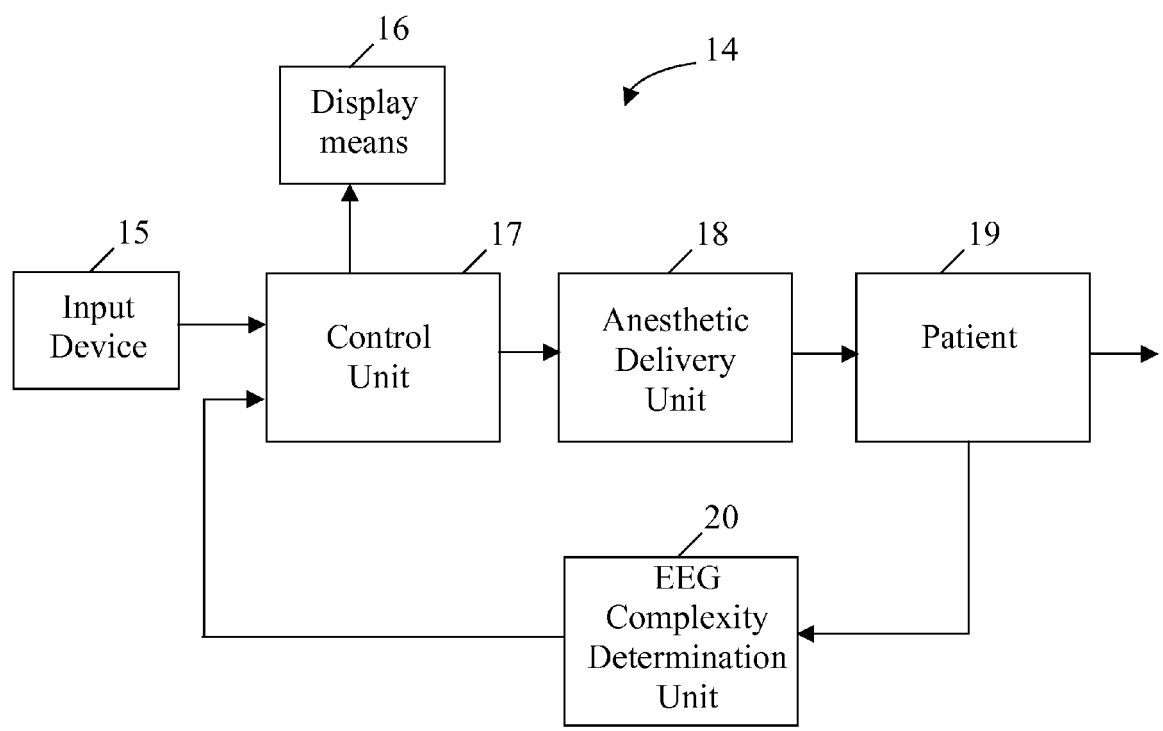
FIG. 3 is a schematic diagram showing one embodiment of a closed loop drug administration control using EEG complexity for control purposes.

FIG. 3 schematically illustrates an embodiment of a system 14 according to the present invention in which a control unit 17 drives an anesthetic delivery unit 18 for supplying an anesthetic drug to patient 19. If the drug is administered intravenously anesthetic delivery unit 18 may comprise a motor driven infusion pump. For hypnotic drugs administered by inhalation, anesthesia delivery unit 18 is typically an electronically controlled vaporizer.

The patient's response and the current anesthetic level of the patient are measured in this example by determining an entropy signal. The entropy signal is determined in the EEG complexity determination unit 20 from the electroencephalographic (EEG) signal and the frontalis electromyographic (FEMG) which are measured by placing electrodes on the forehead of the patient 19. In addition to determining the entropy signal, the EEG complexity determination unit 20 includes modules such as a protection circuit against overdosing, signal processing, and other computational elements e.g. for performing artifact detection and removal. The output from the EEG complexity determination unit 20 is provided to a further input of control unit 17 as shown in FIG. 3 to complete a closed control loop.

The amount of anesthetic drug delivered by anesthetic delivery unit 18 is controlled by the control unit 17, typically by controlling its infusion or administration rate. The control unit 17 is further arranged to direct the anesthetic delivery unit 18 to give the patient small additional boluses as described in FIG. 2 or to momentarily change the infusion rate of the drug to the patient in the negative direction (i.e. reduce the infusion rate momentarily). A detecting unit located either in the EEG complexity determination unit 20 or in the control unit 17 detects the change in the entropy signal that was caused by the change in the infusion rate, and a calculating means calculates the ratio between the change in the entropy signal and the infusion rate change. The ratio describes the sensitivity of the patient 19 to the given drug.

The control unit 17 may be arranged to do this calibration of the patient's sensitivity automatically and periodically, irregularly or at regular intervals. The control unit may also be arranged to inform the user/the anesthesiologist when a new calibration is needed and the user may initiate the giving of the additional bolus. It is also possible for the user to be responsible for carrying out the calibration procedure, or the calibration may be performed automatically each time the anesthesiologist gives the patient a bolus of the drug to change the depth of anesthesia. The display unit 16 may show the user the calculated sensitivity of the patient at that particular moment. And, since the sensitivity of the patient may vary during the surgery individually, it is important that the calibration is repeated e.g. before altering the depth of anesthesia. The input device 15 may also be arranged to receive a desired level for the anesthetic depth. As a response to the desired level given by the user, the required infusion rate change may be displayed to the anesthesiologist. The infusion rate change can be done automatically so that the user merely inputs a desired level of anesthesia or a desired infusion rate and the control unit 17 controls the anesthetic delivery unit 18 until an appropriate anesthesia level is achieved by using the feedback loop of FIG. 3. The user may also be displayed the required change in the infusion rate and he/she can control the infusion rate manually from an appropriate control button in the input device 15.

The required infusion rate change is calculated using the most recently calculated sensitivity parameter calibrated by the apparatus. This sensitivity value gives the most reliable result for the infusion rate change which will result in the desired level of anesthesia. Respectively, the anesthesiologist may input the suggested infusion rate change to the display unit 16 and the display unit will determine the level that will result from such an infusion rate or such a change in the infusion rate. Any bolus and infusion rate change that the anesthesiologist administers to change the anesthetic level, can be used to update the sensitivity calibration.

Although the above examples relate closely to monitoring and controlling the depth of anesthesia during anesthetization, it must be contemplated that the drug may be any other drug such as a muscle relaxant, blood pressure drug or any such drug that causes a measurable change in the patient's body. It should also be noted that respectively, the signal responsive to the drug may be any such signal that changes in response to the given drug, such as muscle relaxation, blood pressure or another signal representing the depth of anesthesia (e.g. Bispectral Index). In addition, there are several other drugs and their response signals not mentioned in this application, but that can be considered similar.

It wilt also be evident to a person skilled in the art that with the advancement of technology, the basic idea of the invention may be implemented in various other ways. The invention and its embodiments are thus not limited to the examples described above; instead they may vary within the scope of the claims.

The invention claimed is:

1. A method for calculating a current sensitivity of a subject to administration of an anesthetic drug during surgery, said method comprising the steps of:
    changing an infusion rate of the drug by a calibration amount during surgery for calibration, in addition to a therapeutic infusion of the drug;
    detecting a change in an entropy signal in response to the infusion rate change; and
    determining a current sensitivity of the subject to the drug based on the change in the entropy signal wherein the current sensitivity has a value defined by a ratio comprising the change in the entropy signal and the change in the infusion rate.

2. The method according to claim 1, further comprising the step of:
    adjusting a delivery rate of the drug based on the current sensitivity of the subject.

3. The method according to claim 1, wherein said entropy signal is derived from an electroencephalogram (EEG) signal.

4. The method according to claim 1, wherein said entropy signal is derived from an electroencephalogram (EEG) signal and a frontalis electromyographic (FEMG).

5. The method according to claim 1, further comprising calculating the infusion rate change corresponding to a desired anesthesia level.

6. The method according to claim 1, further comprising calculating the calibration amount corresponding to a desired anesthesia level.

7. The method according to claim 1, wherein the method further comprises:
    automatically initiating the calibration of the subject's sensitivity to the drug.

8. The method according to claim 1, wherein the method further comprises:
    calibrating the subject's sensitivity to the drug at given intervals.

9. A method according to claim 1, wherein the method further comprises the step of:
    setting at least one safety limit so that the subject is never given the drug over the safety limit.

* * * * *

UNITED STATES PATENT AND TRADEMARK OFFICE
CERTIFICATE OF CORRECTION

PATENT NO. : 8,512,273 B2
APPLICATION NO. : 11/680328
DATED : August 20, 2013
INVENTOR(S) : Rantala et al.

Page 1 of 1

It is certified that error appears in the above-identified patent and that said Letters Patent is hereby corrected as shown below:

In the Specification

In Column 2, Line 65, delete "operations" and insert -- operations, --, therefor.

In Column 5, Line 2, delete "rate I" and insert -- rate 1 --, therefor.

In Column 5, Line 42, delete "form" and insert -- from --, therefor.

In Column 8, Line 6, delete "wilt" and insert -- will --, therefor.

Signed and Sealed this
Fifteenth Day of October, 2013

Teresa Stanek Rea
*Deputy Director of the United States Patent and Trademark Office*